United States Patent
Smalling

(10) Patent No.: US 10,188,409 B2
(45) Date of Patent: Jan. 29, 2019

(54) ASPIRATION THROMBECTOMY CATHETER SYSTEM, AND ASSOCIATED METHODS

(71) Applicant: Smalling Medical Ventures, LLC, Springfield, MO (US)

(72) Inventor: Ronnie G. Smalling, Overland Park, KS (US)

(73) Assignee: Smalling Medical Ventures, LLC, Overland Park, KS (US)

( * ) Notice: Subject to any disclaimer, the term of this patent is extended or adjusted under 35 U.S.C. 154(b) by 486 days.

(21) Appl. No.: 14/553,636

(22) Filed: Nov. 25, 2014

(65) Prior Publication Data

US 2015/0080853 A1 Mar. 19, 2015

Related U.S. Application Data

(63) Continuation of application No. 11/650,628, filed on Jan. 6, 2007, now abandoned.

(60) Provisional application No. 60/757,790, filed on Jan. 9, 2006.

(51) Int. Cl.
*A61M 25/00* (2006.01)
*A61B 17/22* (2006.01)

(52) U.S. Cl.
CPC ........... *A61B 17/22* (2013.01); *A61M 25/003* (2013.01); *A61M 25/007* (2013.01); *A61B 2017/22079* (2013.01); *A61B 2017/22082* (2013.01); *A61B 2017/22084* (2013.01); *A61B 2217/005* (2013.01); *A61M 25/0068* (2013.01); *A61M 2025/0031* (2013.01); *A61M 2025/0037* (2013.01); *A61M 2025/0081* (2013.01)

(58) Field of Classification Search
CPC .............. A61M 1/0084; A61M 1/0064; A61M 1/0047; A61M 5/365; A61B 17/3203; A61B 17/32037; A61B 2217/007
See application file for complete search history.

(56) References Cited

U.S. PATENT DOCUMENTS

| | | | |
|---|---|---|---|
| 2,220,493 A * | 11/1940 | Pixler | A61M 1/008 210/239 |
| 2,286,462 A | 6/1942 | Chaffin | |
| 3,426,759 A | 2/1969 | Smith | |
| 4,400,168 A | 8/1983 | Buechel et al. | |

(Continued)

*Primary Examiner* — Bhisma Mehta
*Assistant Examiner* — Matthew A Engel
(74) *Attorney, Agent, or Firm* — Lathrop Gage L.L.P.

(57) ABSTRACT

An aspiration thrombectomy catheter system includes an aspirator and an aspiration catheter for insertion in a blood vessel. The catheter has a shaft with a proximal end for connection with the aspirator and a tapering distal end with a tip for insertion in the vessel. A plurality of aspiration ports are arranged in sets along the tapering distal end, for aspirating thrombus from the vessel. At least one aspiration lumens within the shaft conducts thrombus from the vessel, through the aspiration ports, to the aspirator. Variably sized or shaped ports provide differing aspiration vectors for enhanced thrombus removal. The aspiration thrombectomy catheter additionally provides for uniform drug dispersion at a thrombotic area, alone or in combination with aspiration of the thrombus. In the event of an adverse reaction, drug dosage may be easily reduced by aspirating dispersed drugs back into the catheter.

6 Claims, 5 Drawing Sheets

(56) References Cited

U.S. PATENT DOCUMENTS

| | | | | |
|---|---|---|---|---|
| 4,767,404 A * | 8/1988 | Renton | A61M 1/008 | 433/93 |
| 5,114,423 A * | 5/1992 | Kasprzyk | A61B 18/08 | 604/913 |
| 5,163,433 A * | 11/1992 | Kagawa | A61B 17/22012 | 601/2 |
| 5,236,414 A * | 8/1993 | Takasu | A61B 17/22012 | 601/3 |
| 5,244,458 A * | 9/1993 | Takasu | A61M 1/0056 | 604/22 |
| 5,419,767 A * | 5/1995 | Eggers | A61B 18/1492 | 604/114 |
| 5,496,267 A * | 3/1996 | Drasler | A61B 17/32037 | 604/22 |
| 5,766,194 A * | 6/1998 | Smith | A61B 17/3203 | 606/1 |
| 5,832,920 A | 11/1998 | Field | | |
| 5,833,644 A * | 11/1998 | Zadno-Azizi | A61B 17/22 | 604/101.05 |
| 5,947,988 A * | 9/1999 | Smith | A61B 17/3203 | 604/22 |
| 6,071,260 A * | 6/2000 | Halverson | A61B 17/320068 | 604/22 |
| 6,106,516 A * | 8/2000 | Massengill | A61B 17/3203 | 606/15 |
| 6,126,631 A * | 10/2000 | Loggie | A61M 25/0026 | 604/264 |
| 6,129,701 A * | 10/2000 | Cimino | A61M 1/0047 | 604/30 |
| 6,135,991 A * | 10/2000 | Muni | A61B 17/22 | 604/22 |
| 6,379,326 B1 * | 4/2002 | Cimino | A61M 1/0047 | 604/30 |
| 6,540,713 B1 * | 4/2003 | Cimino | A61M 1/0047 | 604/30 |
| 6,676,677 B2 * | 1/2004 | Klein | A61B 17/320783 | 604/22 |
| 6,814,718 B2 * | 11/2004 | McGuckin, Jr. | A61M 1/285 | 604/107 |
| 7,211,073 B2 * | 5/2007 | Fitzgerald | A61B 5/0086 | 128/898 |
| 7,300,429 B2 * | 11/2007 | Fitzgerald | A61B 5/0084 | 604/500 |
| 7,530,976 B2 * | 5/2009 | MacMahon | A61M 1/0009 | 604/121 |
| 8,052,672 B2 * | 11/2011 | Laufer | A61B 17/320016 | 604/542 |
| 8,562,555 B2 * | 10/2013 | MacMahon | A61M 1/0009 | 604/264 |
| 9,510,894 B2 * | 12/2016 | Clark | A61B 18/14 | |
| 2001/0044591 A1 * | 11/2001 | Stevens | A61M 1/3659 | 604/6.11 |
| 2002/0177800 A1 * | 11/2002 | Bagaoisan | A61B 17/22 | 604/6.12 |
| 2003/0040736 A1 * | 2/2003 | Stevens | A61M 1/3659 | 604/532 |
| 2004/0133232 A1 | 7/2004 | Rosenbluth et al. | | |
| 2004/0210187 A1 * | 10/2004 | Zawacki | A61M 1/3653 | 604/43 |
| 2004/0215222 A1 | 10/2004 | Krivoruchko | | |
| 2004/0254523 A1 * | 12/2004 | Fitzgerald | A61B 5/0086 | 604/21 |
| 2005/0085769 A1 * | 4/2005 | MacMahon | A61M 1/0009 | 604/96.01 |
| 2005/0124969 A1 * | 6/2005 | Fitzgerald | A61B 5/0084 | 604/508 |
| 2008/0091166 A1 * | 4/2008 | Fitzgerald | A61B 5/0084 | 604/500 |
| 2008/0097339 A1 * | 4/2008 | Ranchod | A61M 25/007 | 604/246 |
| 2008/0275393 A1 * | 11/2008 | Bonnette | A61B 17/22 | 604/102.01 |

* cited by examiner

ASPIRATION THROMBECTOMY CATHETER SYSTEM, AND ASSOCIATED METHODS

RELATED APPLICATIONS

This application is a continuation of U.S. patent application Ser. No. 11/650,628, filed Jan. 6, 2007 which claims priority of U.S. Provisional 60/757,790, filed Jan. 9, 2006, which are incorporated herein by reference.

BACKGROUND

Coronary artery thrombus may be a cause of, or a culprit in, acute coronary syndromes such as acute myocardial infarction and unstable angina. The presence of thrombus in the coronary artery, accompanying a significant artherosclerotic plaque narrowing, complicates optimal revascularization by percutaneous techniques such as angioplasty or stenting.

Distal embolization of thrombus into the distal coronary artery macro and micro circulation, which may for example occur during balloon angioplasty or coronary stenting, results in reduced TIMI (Thrombolysis in Myocardial Infarction) flow. Reduced TIMI flow or flow grade has been demonstrated to reduce patient outcomes in such studies as the PAMI (Primary Angioplasty in Myocardial Infarction) stent trials and the CADILLAC (Controlled Abciximab and Device Investigation to Lower Late Angioplasty Complications) clinical trials.

Dealing with coronary thrombus in these situations has been the subject and focus of many pharmacologic and endovascular techniques. Endovascular techniques of thrombus removal by thrombectomy devices have been well studied and several existing devices have been tried, such as the Possis AngioJet® System, which theoretically allows a physician to infuse medication directly into a thrombus and/or remove the thrombus through power pulse aspiration. Unfortunately, clinical trials conducted with the AngioJet® System have failed to demonstrate an advantage over previous techniques for treating coronary thrombus, such as balloon angioplasty prior to implantation of a stent.

Other means of treating coronary thrombus include passive aspiration by end-hole aspiration thrombectomy catheters such as the Export aspiration catheter. The Export aspiration catheter consists of a 5 French monorail catheter connected to an evacuated 20 ml syringe used to remove thrombotic debris. While rather extensively used, the efficacy of this treatment is limited by thrombus plugging the end hole during the procedure. Other, newer passive aspiration catheters like the Diver CE (manufactured by V3, Inc.) include a few side holes along the catheter body near the end of the aspiration catheter; yet such catheters are apt to plug with only slightly more thrombus than necessary to plug the passive export catheter.

SUMMARY

The aspiration thrombectomy catheter system disclosed herein may overcome problems associated with prior devices to provide thrombus removal and drug dispersion in coronary arteries or arterial conduits, such as saphenous vein bypass grafts or peripheral arteries.

In one embodiment, an aspiration thrombectomy catheter system includes an aspirator and an aspiration catheter for insertion in a blood vessel. The aspiration catheter has a shaft with (a) a proximal end for connection to the aspirator and (b) a tapering distal end with a tip for insertion in the vessel. A plurality of aspiration port sets, each having a plurality of ports for aspirating thrombus from the vessel, are arranged along the tapering distal end. At least one aspiration lumens within the shaft conducts thrombus from the vessel, through the aspiration ports, to the aspirator.

In one embodiment, a method for aspirating thrombus includes advancing an aspiration catheter within a vessel until at least a distal set of aspiration arranged along a distal portion of tapering catheter tip is proximate a thrombus. Aspiration forces are applied through at least the distal set of aspiration ports to suction at least a first portion of the thrombus into a first aspiration lumens. The aspiration catheter is advanced through unaspirated thrombus and aspiration forces are applied via at least one second set of aspiration ports arranged proximal to the distal set of aspiration ports, along the tapering catheter tip, to suction at least a second portion of the thrombus into the aspiration catheter.

In one embodiment, a method for aspirating thrombus includes advancing an aspiration catheter within a vessel to an occluding thrombus. One or more lytic agents are dispersed from a first catheter lumens to the thrombus via a first set of ports opening into the first catheter lumens. Aspiration forces are applied to the thrombus via at least a second set of ports, the second set of ports conducting aspirated thrombus into a second catheter lumens.

DETAILED DESCRIPTION

It is appreciated that the present teaching is by way of example, not limitation. The illustrations herein are not limited to use or application with a specific type of aspiration thrombectomy catheter. Thus, although the instrumentalities described herein are for the convenience of explanation, shown and described with respect to exemplary embodiments, it is appreciated that the principals herein may be equally applied in other embodiments of aspiration thrombectomy catheters.

For example, for ease of discussion, aspiration thrombectomy catheter system 100 is described herein below with respect to removal of coronary thrombus; however, those skilled in the art will recognize, after reading and fully appreciating the present disclosure, that system 100 may be equally applied for enhanced thrombus removal elsewhere in the circulatory system. For example, system 100 may be applied in:

Removal of thrombus in the carotid circulation, both extra-cranial and intra-cranial;
Removal of visceral thrombus, for example from arteries supplying digestive organs and/or from arteries supplying the kidneys;

Removal of peripheral vascular thrombus, for example from the legs;

Thrombus removal in surgically created arterial venous fistulas for hemodialysis, for example using cross-catheter thrombectomy;

Removal of thrombus from synthetic dialysis access grafts;

Removal of thrombus from surgically created synthetic or native vein bypass grafts (both harvested and transplanted and in-situ vein grafts);

Removal of thrombus from a stent;

Removal of stenosis from a stent or surgically created fistula, dialysis access or vein bypass graft;

Isolated and uniform drug dispersion through aspiration ports, e.g., during any of the above procedures; and Readily customizable dosage (e.g., amplification and/or reduction) as a function of real-time patient response to dispersed drugs.

As used herein, the term "vessel" refers to any circulatory conduit, including but not limited to the aforementioned arteries, veins, fistulas, grafts and stents.

Figure 1:
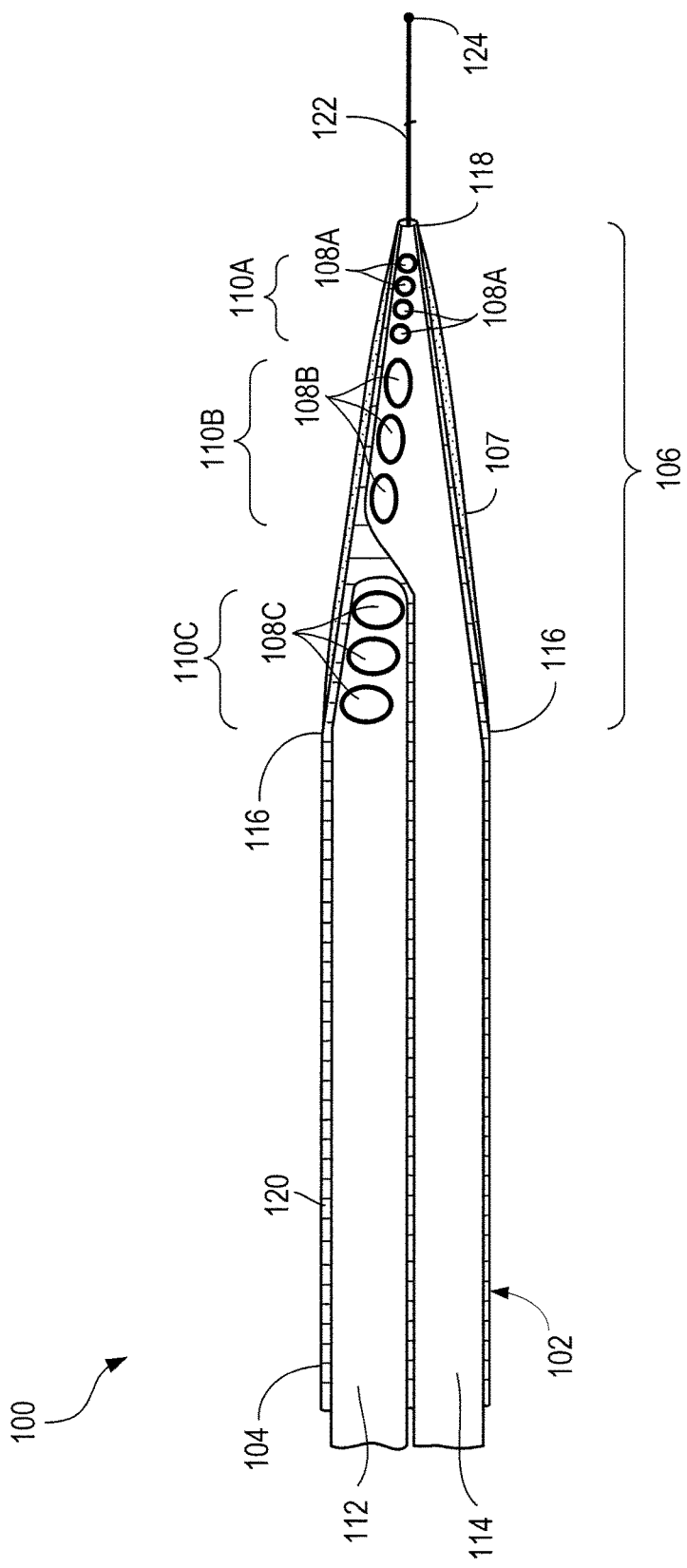
FIG. 1 depicts one embodiment of an aspiration thrombectomy catheter system including an aspiration thrombectomy catheter.

FIG. 1 shows an aspiration thrombectomy catheter system 100. System 100 includes a catheter 102 having a shaft 104. Shaft 104 has one or more proximal ends (not shown; see however FIG. 4) for connection with one or more aspirators, and a distal end or section 106. As shown in FIG. 1, a distal end 106 has a plurality of aspiration holes or ports 108, arranged in a plurality of sets 110. As used herein, a set of ports indicates two or more ports grouped in close proximity to one another. In one embodiment, distal section 106 includes three sets 110A-110C having ports 108A-C, respectively. Sets 110A-C may be arranged as distal set 110A, middle set 110B and proximal set 110C, with respective ports 108A (distal ports), 108B (middle ports) and 108C (proximal ports) opening into one or more aspiration port channels/lumens.

Distal end/section 106 of catheter 102 is for example inserted into the circulatory system on a needle and advanced to an occlusion in a small, medium or large artery; therefore, system 100 may be sized for the desired use (as used herein, the terms "occlusion" and "occluding" may refer to partial or complete occlusion or occluding of a vessel). Distal section 106, and optionally all or a portion of shaft 104, may be formed or coated with a smooth or low-friction material such as Teflon, to facilitate advancement of catheter 102. Further, catheter 102 may be configured as a single or a dual aspiration catheter. When catheter 102 is a single lumen aspiration catheter, an aspirator attaches to the proximal end of the catheter. When catheter 102 is a dual lumen aspiration catheter, shaft 104 branches to form two proximal ends for connection with one or more aspirators.

Distal section 106 tapers proximally to distally from a shoulder 116 to a tip 118. Tip 118 and/or a portion or all of distal section 106 is for example formed or covered with a soft material 107 to minimize vessel trauma, while part or all of shaft 104 is stiffer, to prevent kinking and facilitate advancement and torqueability of catheter 102 within a vessel, such as a coronary artery. Walls 120 of shaft 104, and optionally distal section 106, for example include medically acceptable rigid polymers, co-polymers or metals, such as plated or unplated stainless steel, ELGILOY, platinum, a shape-memory alloy such as nitinol, or combination thereof. In one embodiment, shaft 104 is a flexible tube reinforced with one or more of the above polymers, co-polymers and/or metals. Such reinforcement materials may be wired, braided or coiled through or within shaft 104. Proximal-to-distal flexibility may be increased by decreasing braid, coil or wire density from proximal end/s to distal section 106 or tip 118. A degree of reinforcement within distal section 106 for example provides for a soft-tipped catheter 102 that resists twisting or wrapping of tip 118 and/or distal section 106 during advancement or rotation.

Figure 2:
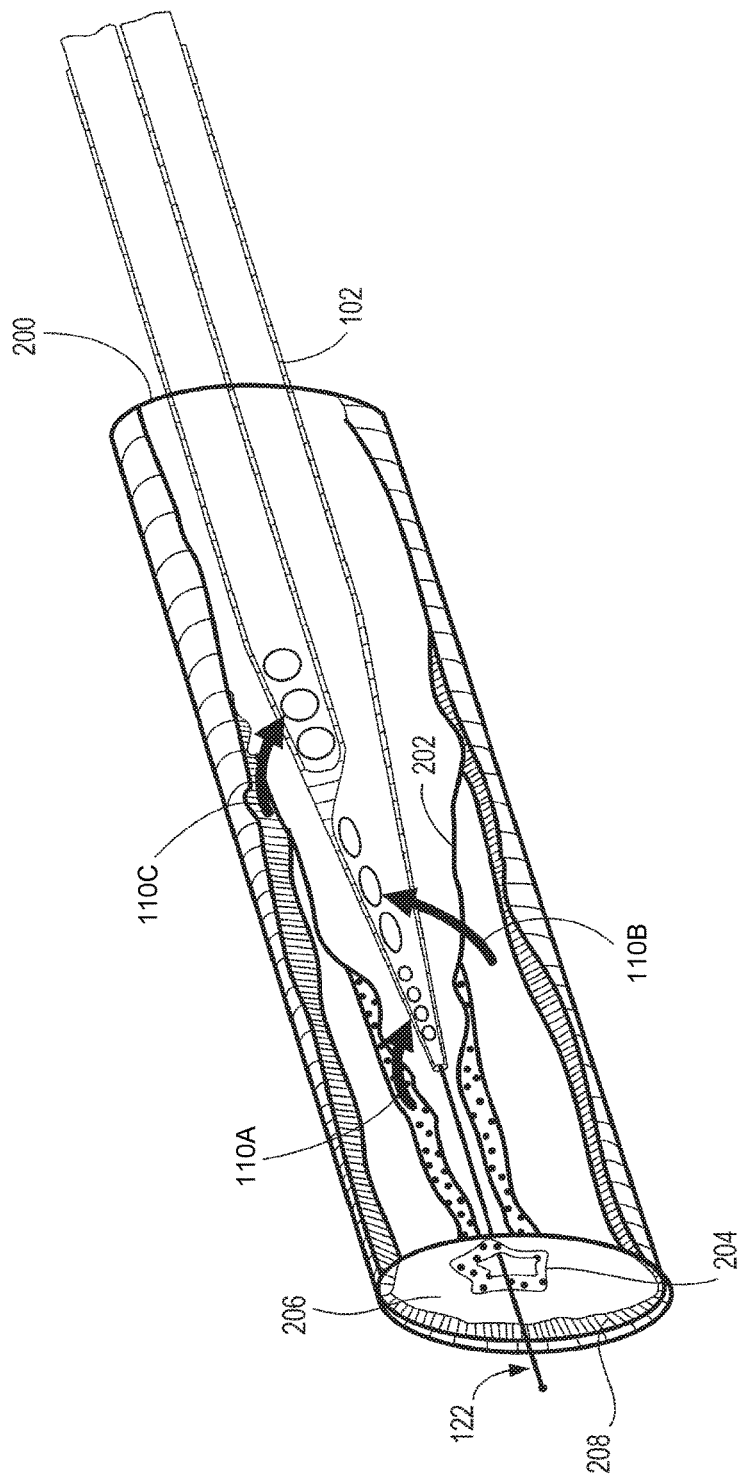
FIG. 2 shows the aspiration thrombectomy catheter of FIG. 1 in a section of artery.

A wire 122 guides catheter 102 in a vessel, e.g., artery 200, FIG. 2. Catheter 102 may be a monorail or fixed wire catheter (e.g., to allow for smaller diameters) or an over-the-wire catheter. That is, wire 122 may be fixed with catheter tip 118, with a set distance between tip 118 and a wire tip 124, or catheter wire 122 may be a separate and unattached guide wire over which catheter 102 rides.

In one embodiment, catheter 102 is an over-the-wire catheter (for ease of illustration, the wire lumen of the catheter is not shown). Over-the-wire catheters often ride in the center of straight segments of an artery. As catheter 102 advances into an arterial thrombus, vacuum forces provided at a certain magnitude through ports 108A-C of tapering distal section 106 aspirate thrombus, for example from the inside-out, via ports 108A, 108B and 108C. As distal section 106 encounters thrombus, vacuum forces provided through ports 108A aspirate nearby thrombus. As thrombotic material is generally cohesive, thrombus drawn into ports 108A (and/or 108B, 108C) may pull additional thrombus into catheter 102. Portions of thrombus that are not pulled into catheter 102 by cohesion, e.g., portions that are too far away for aspiration through ports 108A, may be drawn inward and closer to middle and/or proximal ports 108B, 108C, by vacuum forces. As middle/proximal ports 108B, 108C are positioned on wider portions of distal end 106 than ports 108A, aspiration is further facilitated as catheter 102 advances within the vessel and the distance between the vessel walls and adhered thrombus, and ports 108A-108C successively decreases. Increased proximity between remaining thrombus and ports 108B, 108C (e.g., provided both by inward pull through ports 108A and the taper of distal section 106), for example allows the same magnitude of vacuum force applied through distal ports 108A to effectively aspirate remaining thrombus through ports 108B, 108C. The effective surface area of thrombus aspirated is thereby increased.

The tapering design of catheter 102 may further provide increased thrombus-to-port contact or proximity over the prior art. For example, prior art French catheters have essentially the same diameter from proximal end to distal end. Aspiration ports of such a prior art catheter are therefore located farther and farther from remaining, unaspirated thrombus as the catheter advances in the artery. A prior art catheter of essentially uniform diameter may be unable to effectively remove intimal thrombus, whereas the tapering design of catheter 102 provides increasing proximity between distal-to-proximal aspiration ports and medial-to-intimal thrombus, respectively, as catheter 102 advances therethrough. For example, thrombus that is pushed or wedged away from distal aspiration ports, such as ports 108 (e.g., pushed against the vessel wall by a guide wire or fixed wire) may be aspirated via middle or proximal ports 108B, 108C of catheter 102, whereas the prior art French catheter may be unable to aspirate the displaced thrombus due to the increased port-to-thrombus distance. In addition, Catheter shoulder 116 may trap unaspirated thrombus, providing an extended opportunity for aspiration through proximal ports 108C, e.g., during withdrawal of the catheter.

As shown in FIG. 1, catheter 102 has a proximal, or first aspiration lumens 112 (hereinafter referred to as first lumens 112) for aspiration through proximal ports 108C, and a middle-distal, or second aspiration lumens 114 (hereinafter referred to as second lumens 114) for aspiration through middle and distal ports 108B, 108A. Distal, middle and proximal ports 108A, 108B and 108C may be sized, shaped and/or oriented differently from one another. FIG. 1 illustrates round distal ports 108A and elliptical middle and proximal ports 108B, 108C of differing size and orientation. However, other arrangements of port shapes and sizes are within the scope hereof. For example, all of ports 108A-C may be elliptical, with ports 108B, 108C of middle and proximal sets 110B, 110C differing in orientation and/or size from distal ports 108A of set 110A. Alternately, ports of sets 110A-C may be similarly sized and shaped, but differently oriented. Such variation in port size, shape and/or orientation provide system 100 with a variety of vortices and aspiration vector forces (directions and/or magnitudes), for enhanced thrombus removal over prior art catheters having fewer ports of essentially the same size, shape and orientation. Sets of small ports for example enhance aspiration by the Venturi effect, speeding flow of aspirated thrombus into aspiration lumens 112/114, while larger port sets allow for aspiration of larger thrombotic particles.

FIG. 2 shows system 100 in a section of artery 200 partially occluded by thrombus 202. As wire 122 and catheter 102 advance through thrombus 202, aspiration port sets 110A-110C successively contact or come into proximity with innermost, middle and intimal layers 204, 206, 208 of thrombus 202. Aspiration of innermost, middle and intimal layers 204-208 may occur as illustrated by directional aspiration arrows 210. Aspiration is facilitated by increased thrombus-to-port contact or proximity provided by catheter 102, thus facilitating removal of a greater thrombus burden as the catheter advances through the vessel. The plurality of ports 108A-C may also minimize plugging by organized or large thrombus aggregates, as is seen with prior art end-hole catheters or prior art catheters having fewer side ports.

The tapered design of catheter 102 may reduce distal embolization of thrombus. For example, as a catheter advances through thrombus, portions of the thrombus may be loosened, but not aspirated. Prior art designs having substantially uniform catheter or distal section diameter may not come into close enough proximity to aspirate portions of thrombus clinging to the intima, for example; however, this intimal thrombus may be loosened. The loosened thrombus may break free and embolize in distal arterial conduits. The tapering shaft of catheter 102 may reduce this distal embolization because aspiration ports 108A-C come closer to the vessel walls and any thrombus clinging thereto as the catheter advances. Thrombus loosened during aspiration by ports 108A or 108B is for example aspirated when ports 108C come into proximity or contact with the loosened thrombus.

System 100 may also enhance thrombectomy when utilized in a curved section of artery. Aspiration port sets 110A-C approach thrombus on an arterial wall in closer and closer succession, due to the tapering design of catheter 102. Thus, catheter 102 may thus also remove thrombus 202 medially-to laterally in a curved section of artery, as described herein above with respect to FIG. 2.

Figure 3:
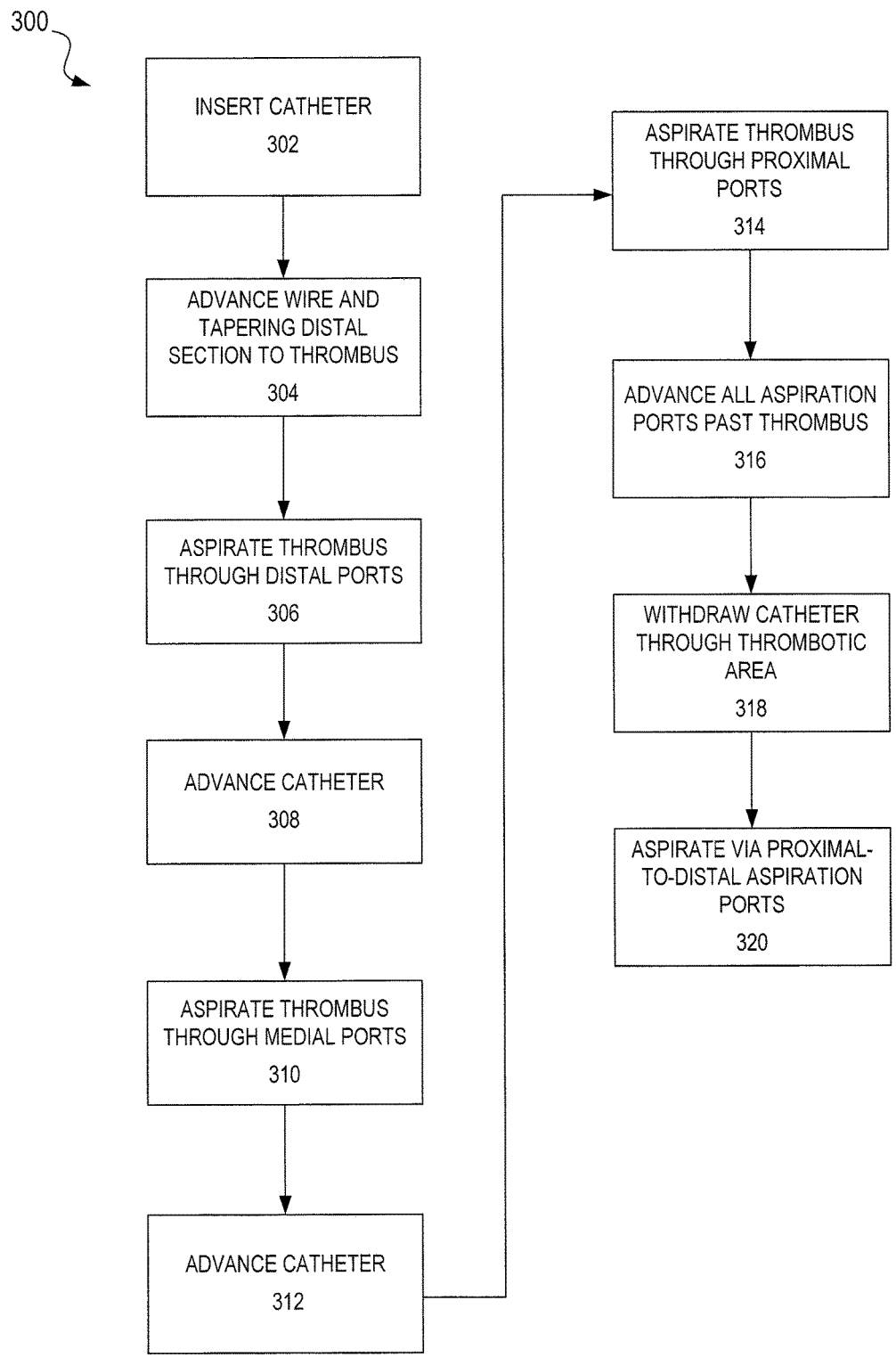
FIG. 3 is a flow-chart illustrating a method of aspirating thrombus, for example using the aspiration thrombectomy catheter of FIG. 1.

FIG. 3 is a flow chart illustrating a method 300 of aspirating thrombus. An aspiration catheter, such as catheter 102 on wire 122, is inserted into an artery, in step 302. A tapering distal end of the catheter, e.g., end 106 of catheter 102, is advanced into the thrombus, in step 304. Thrombus is aspirated through distal aspiration ports of the catheter and through an aspiration lumens, for example ports 108A and second lumens 114, in step 306. As the catheter is advanced further into the blocked artery, middle ports such as ports 108B are brought into contact with or proximal to unaspirated portions of the thrombus, in step 308. These portions are aspirated through an aspiration lumens, such as second lumens 114, via the middle ports, in step 310. Catheter 102 is advanced yet further into the blocked artery, such that proximal ports of the catheter, e.g., ports 108C, are brought into contact with or proximal to remaining portions of the thrombus that were not aspirated through the middle ports, in step 312. These remaining portions of thrombus are aspirated through an aspiration lumens such as first lumens 112, via the proximal aspiration ports, in step 314.

Continued aspiration during withdrawal of catheter system 100 may further enhance thrombus removal. Once the catheter has traveled past thrombus, it may aspirate remaining thrombus during withdrawal back through the artery. Catheter 102 may, for example, trap remaining thrombus between the catheter shoulder 116 or shaft 104 and the arterial wall during an antegrade pass. The trapped thrombus may then be aspirated through proximal-to-distal ports 108C-108A as the catheter is withdrawn. Accordingly, the catheter is advanced until aspiration ports (such as port sets 110A-110C) have passed through the thrombus, in step 316. The catheter is withdrawn back through any remaining thrombus, in step 318. The proximal, middle and distal aspiration ports aspirate remaining thrombus, in step 320.

Steps 302-320 need not be performed in the order described in connection with FIG. 3. For example, thrombus may be aspirated through aspiration ports while catheter 102 is simultaneously and continually advanced through a thrombus. Also, not all of steps 302-320 need necessarily be performed for effective thrombus removal. For example, if thrombus is completely removed during an antegrade pass therethrough, it may not be necessary to aspirate while withdrawing catheter 102.

Figure 4:
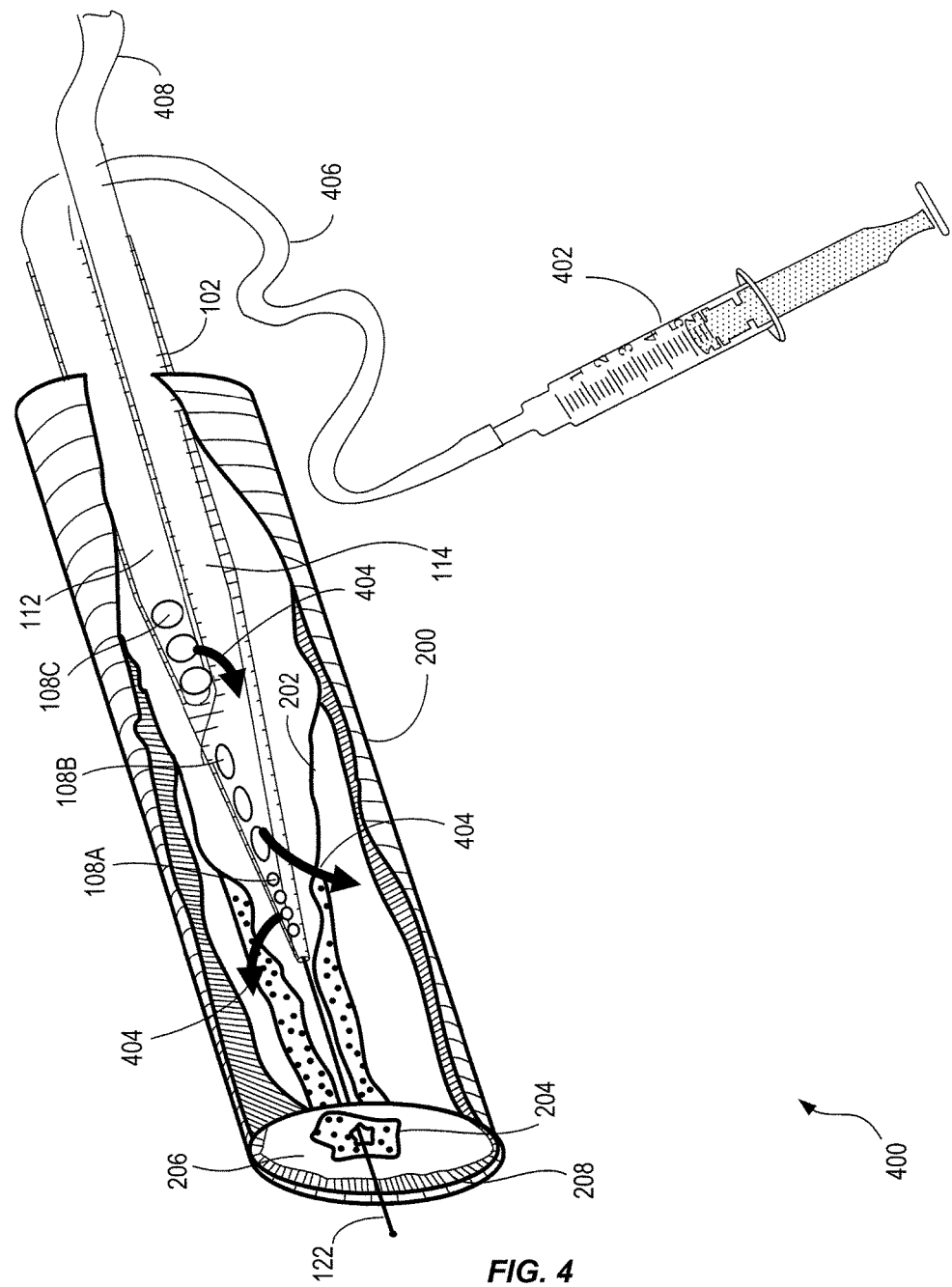
FIG. 4 illustrates drug dispersion proximate a thrombus, with the aspiration thrombectomy catheter of FIGS. 1 and 2.

The proximal end or ends of catheter 102 are connectable with an infusion device, such as a syringe, allowing use of thrombectomy catheter system 100 in thrombolysis, for example to lyse deep and superficial venous thrombi, or in cross-catheter thrombolysis in surgically created arterial venous fistulas. A lytic agent or agents, e.g., Reteplase or Alteplase, is infused via aspiration lumens 112 and/or 114, for precise and uniform dispersion through ports 108A-108C. FIG. 4 depicts an aspiration thrombectomy catheter system 400 for removing thrombus from partially occluded vessel 200. Vessel 200 is for example blocked by thrombus 202 as described above with respect to FIG. 2. Catheter 102 is inserted into vessel 200 and advanced to thrombus 202. Catheter 102 may again be an over-the-wire or a fixed wire catheter. In one embodiment, catheter 102 is a fixed wire or monorail catheter 102, with wire 122 securely formed with catheter tip 118 (see FIG. 1). Wire 122 guides distal section 106 to and/or partially through thrombus 202, where aspiration may be applied as previously described.

Optionally or additionally, catheter 102 connects to a drug dispenser or drug delivery apparatus, such as a gravity flow system, an automated or manually operable pump, a syringe or other intravenous drug dispenser. Such a dispenser is illustratively shown in FIG. 4 as a syringe 402 (not to scale). Once distal section 106 is positioned as desired, relative to the thrombus, lytic agents are for example delivered through lumens 112 and/or 114 and out one or more of port sets 110A-110C, as indicated by dispersion arrows 404. System 400 thus provides isolated drug delivery with uniform dispersion from each port 108A-108C, at the occluded/thrombotic area. Alternately, system 400 provides targeted drug delivery via selected ports or port sets 108, 110, while remaining ports or port sets may be used in aspirating loosened thrombus, delivering complementary lytic agents, e.g., in sequence, or reducing dosage in the event of overdose or adverse patient reaction.

In one embodiment, lumens 114 connects with or extends into tubing 406 which in turn connects to syringe 402. Tubing 406 for example conducts a thrombolytic, antibiotic or otherwise therapeutic drug from syringe 402, through lumens 114, to proximal ports 108C. Should an adverse reaction such as bleeding occur, dosage may be quickly reduced by aspirating the delivered drug back through proximal ports 108C, for example by drawing back on syringe 402. It will be understood that lumens 112 may likewise connect, via tubing 408, to a drug or lytic agent dispenser or delivery system such as a second syringe, to facilitate delivery of desired drug combinations or sequences, e.g., via middle and distal ports 108B, 108A. Likewise, one of lumens 112, 114 may connect via tubing 406, 408 with an aspirator while the other of lumens 112, 114 connects with the drug dispenser. In the case of an adverse drug reaction, dosage may be quickly reduced by aspirating drugs released via one set of ports 110 back through another set of ports 110. For example, lytic drugs delivered to lumens 114 and dispersed through proximal ports 108C may be aspirated back through distal and middle ports 108A, 108B, in communication with lumens 112. Aspiration thrombectomy catheter system 400 may also be used to alternately or simultaneously disperse lytic agents and remove/aspire thrombus loosened by the lytic agents. Likewise, a combination of ports 108A-C may be used in aspiration or drug dispersion.

Figure 5:
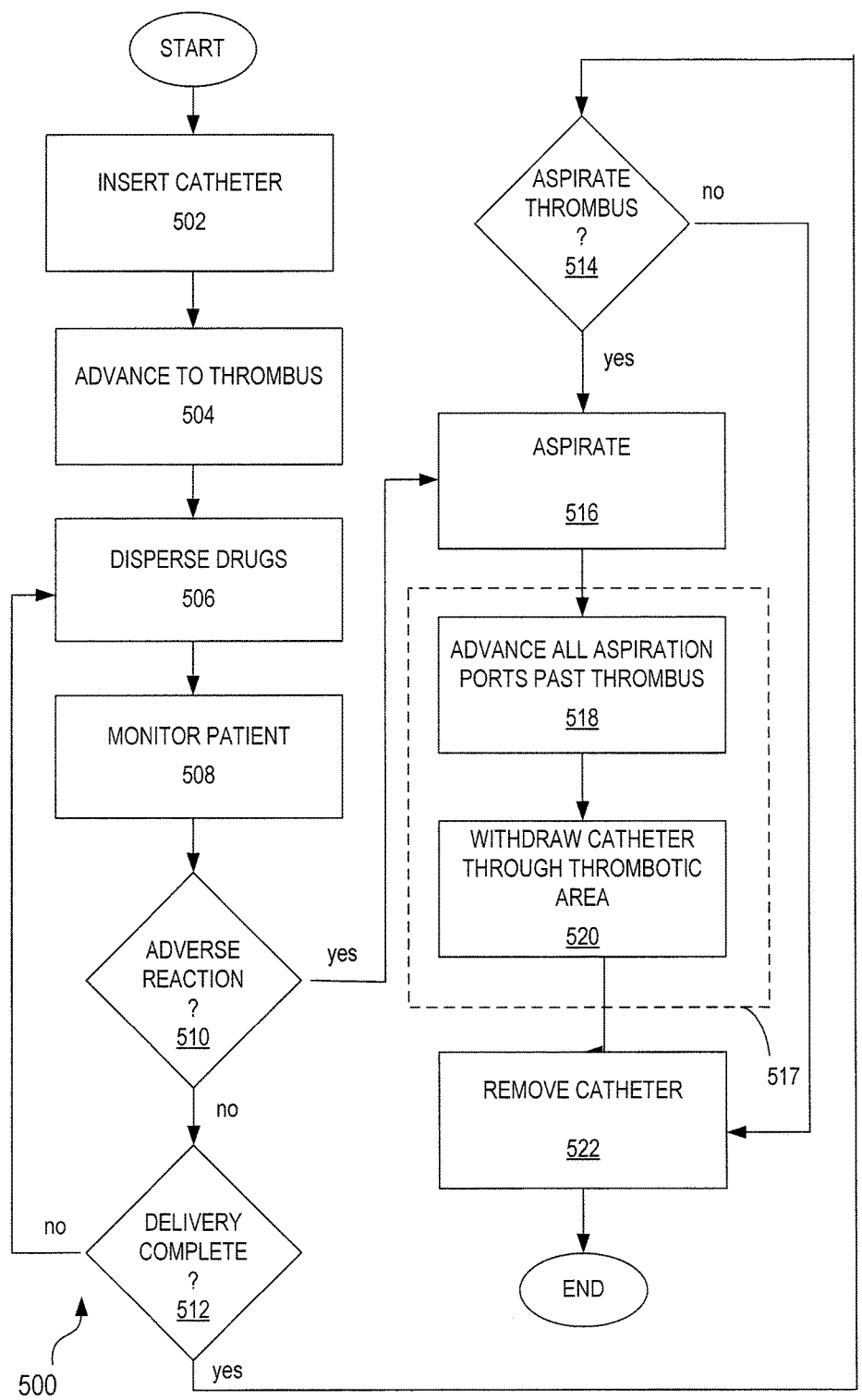
FIG. 5 is a flow-chart showing a method of delivering thrombolytic drugs, for example using the aspiration thrombectomy catheter of FIGS. 1, 2 and 4.

FIG. 5 is a flowchart illustrating one method 500 for removing thrombus with an aspiration thrombectomy catheter. In step 502 an aspiration thrombectomy catheter is inserted into a vessel. In step 504, the catheter is advanced to a thrombus. In one example of steps 502, 504, catheter 102 is inserted into an artery and advanced until distal section 106 contacts or is proximate the thrombus. When the catheter is in position, e.g., distal section 106 is proximate or contacting the thrombus, drugs are dispersed, in step 506. In one example of step 506, drugs are applied to tubing 406 via a drug dispenser. Drugs travel into lumen 112 and out of ports 108C.

The patient undergoing method 500 is monitored, in step 508, e.g., for bleeding or other adverse reactions to lytic drugs. If (decision 510) an adverse reaction occurs, released drugs are aspirated, in step 516. In one example of step 516, upon determining that an overdose or adverse reaction has occurred, released lytic drugs are aspirated back into catheter 102 via distal and medial aspiration ports 108A, 108C. Lumen 114, in contact with ports 108A, 108C, connects with tubing 408 which in turn connects with an aspirator, such as a syringe. The aspirator or syringe is activated to "vacuum" the lytic drugs from the vessel.

Dotted box 517 indicates optional steps during or in combination with aspiration step 516. In optional step 518, the catheter is advanced until all aspiration ports have passed through the thrombus. In step 520, the catheter is withdrawn through the thrombotic area. Steps 518, 520 may be repeated as desired to facilitate aspiration of a thrombolytic agent that has dispersed within the vessel, or to aspirate thrombus loosened by the thrombolytic agent, as described below.

Returning to method 500, if (decision 510) there is no adverse reaction or overdose and if (decision 512) drug delivery is complete, method 500 continues with decision 514. If (decision 514) thrombus is to be aspirated, aspiration commences in step 516. Optional steps 518, 520 may be repeated until the desired or maximum amount of thrombus has been removed from the vessel. In one example of steps 516-520, where aspiration is desirable, tubing 404 is disconnected from the aforementioned drug dispenser or delivery system, e.g., syringe 402, FIG. 4, is switched to an aspiration mode. As catheter 102 is advanced through (step 518) and withdrawn from (step 520) the thrombotic area, vacuum forces are applied via aspiration ports 108A, 108B and 108C until the thrombus is satisfactorily removed from the vessel walls. Once the thrombus is satisfactorily aspirated, the catheter is removed, in step 522. In one example of step 522, catheter 102 is withdrawn from the body of a patient undergoing method 500.

In one example of steps 506-522, a thrombolytic agent is dispersed via distal port set 110A, FIG. 1. As noted, distal port set 110A may open into a lumens independent of the lumen or lumens associated with middle and proximal port sets 110A, 110B. If desired, a second thrombolytic agent is dispersed via middle or proximal port sets 110A, 110B. The second thrombolytic agent may be dispersed synchronously with the agent dispersed via distal ports 108A, or the two agents may be alternated or pulsed to achieve a desired drug combination or amount proximate the thrombus.

When drug delivery, or a drug delivery cycle, is complete, thrombus loosened by drug therapy is for example aspirated as described above, through one or more of port sets 110A-110C. Catheter 102 may be advanced and withdrawn back and forth through the thrombotic region during (or interspersed with) aspiration), to enhance thrombus removal. Catheter 102 may likewise be rotated such that port sets 110A-C along distal section 106 vacuum the entire inner circumference of the vessel. When thrombus is satisfactorily removed, catheter 102 is withdrawn from the patient's body, step 522.

Although not shown in FIG. 5 (for ease of illustration), it will be recognized that drug delivery step 506 and aspiration steps 516-520 may be repeated as desired prior to removal of catheter 102 (step 522). For example, where decision 516 pertains to one of multiple drug delivery cycles, method 500 may move from aspiration steps 516, 518 or 520 back to drug dispersion at step 506.

Changes may be made in the above systems and structures without departing from the scope thereof. It should thus be noted that the matter contained in the above description and/or shown in the accompanying drawings should be interpreted as illustrative and not in a limiting sense. The following claims are intended to cover generic and specific features described herein, as well as all statements of the scope of the present system and structures, which, as a matter of language, might be said to fall therebetween.

The invention claimed is:

1. A method for aspirating a thrombus from a vessel, the thrombus having at least a first portion and a second portion, wherein the first portion is within an innermost layer of the thrombus and the second portion is within a medial or an intimal layer of the thrombus, the method comprising the steps of:
   inserting an aspiration catheter into the vessel, the aspiration catheter having a first lumen and a second lumen disposed therein, a tapering distal end and a plurality of aspiration port sets arranged along the tapering distal end, each of the plurality of aspiration port sets having a plurality of ports for aspirating thrombus from the vessel, and wherein at least one of the plurality of aspiration port sets is in fluidic communication with the first lumen and at least another one of the plurality of aspiration port sets are in fluidic communication with the second lumen;

advancing the aspiration catheter within the vessel until an aspiration port set closest to a tip of the tapering distal end of the aspiration catheter is proximate the first portion of the thrombus;

applying aspiration forces through at least the aspiration port set closest to the tip of the tapering distal end of the aspiration catheter to suction at least the first portion of the thrombus into the first lumen;

advancing the aspiration catheter through the thrombus until the aspiration port set closest to the tip of the tapering distal end of the aspiration catheter is proximate to the second portion of the thrombus; and applying aspiration forces through an aspiration port set disposed closest to a proximal end of the tapering distal end of the aspiration catheter to suction at least the second portion of the thrombus into at least one of the first and second lumens;

wherein each of the plurality of ports comprising the aspiration port set closest to the tip of the tapering distal end of the aspiration catheter is smaller in size than each of the plurality of ports comprising the aspiration port set disposed closest to the proximal end of the tapering distal end of the aspiration catheter.

2. The method of claim 1, further comprising the steps of:
aspirating through the aspiration port set closest to the proximal end of the tapering distal end of the aspiration catheter when it is adjacent to the thrombus;
aspirating through the aspiration port set closest to the tip of the tapering distal end of the aspiration catheter when it is adjacent to the thrombus; and
withdrawing the aspiration catheter through the thrombus while continuing to aspirate remaining thrombus.

3. The method of claim 2, wherein applying aspiration forces through the aspiration port set closest to the tip of the tapering distal end of the aspiration catheter comprises activating a first aspirator and applying aspiration forces through at least one of the first and second lumens.

4. The method of claim 1, further comprising the steps of dispersing lytic agents to the thrombus through at least one of the plurality of aspiration port sets and simultaneously aspirating the thrombus through the other respective plurality of aspiration port sets.

5. The method of claim 1, further comprising the step of dispersing lytic agents to the thrombus through the aspiration port set closest to the tip of the tapering distal end of the aspiration catheter before the step of applying aspiration forces through at least the aspiration port set closest to the tip of the tapering distal end of the aspiration catheter.

6. The method of claim 5 wherein the step of dispersing lytic agents further comprises the step of monitoring for adverse reactions.

* * * * *